United States Patent [19]

Martin, Sr.

[11] Patent Number: 5,588,957
[45] Date of Patent: *Dec. 31, 1996

[54] CERVICAL COLLAR

[75] Inventor: Bill Martin, Sr., Shepherdsville, Ky.

[73] Assignee: Ambu International A/S, Glostrup, Denmark

[ * ] Notice: The term of this patent shall not extend beyond the expiration date of Pat. No. 5,366,438.

[21] Appl. No.: 515,219

[22] Filed: Aug. 15, 1995

Related U.S. Application Data

[63] Continuation of Ser. No. 237,139, May 3, 1994, abandoned, which is a continuation of Ser. No. 64,221, May 20, 1993, Pat. No. 5,336,438.

[51] Int. Cl.$^6$ ............................................. A61F 5/04
[52] U.S. Cl. ................................. 602/18; 128/DIG. 23
[58] Field of Search ............................ 602/4, 5, 17, 187; 128/DIG. 23

[56] References Cited

U.S. PATENT DOCUMENTS

| | | |
|---|---|---|
| Re. 32,219 | 8/1986 | Garth . |
| 2,102,069 | 12/1937 | Hanicke . |
| 2,692,595 | 10/1954 | Blair, Jr. . |
| 2,735,424 | 2/1956 | Benjamin . |
| 2,736,314 | 2/1956 | Hale . |
| 2,801,630 | 8/1957 | Moore . |
| 2,806,471 | 9/1957 | Breese . |
| 2,807,260 | 9/1957 | Teufel . |
| 2,818,063 | 12/1957 | Smith et al. . |
| 2,820,455 | 1/1958 | Hall . |
| 2,828,736 | 4/1958 | Monfardini . |
| 2,904,040 | 9/1959 | Hale . |
| 2,911,970 | 11/1959 | Bartels . |
| 3,024,784 | 3/1962 | Monfardini . |
| 3,027,894 | 4/1962 | Moore . |
| 3,042,026 | 7/1962 | Monfardini . |
| 3,042,027 | 7/1962 | Monfardini . |
| 3,050,052 | 8/1962 | Grassl . |
| 3,055,358 | 9/1962 | Di Palma et al. . |
| 3,070,090 | 12/1962 | Taylor . |
| 3,075,521 | 1/1963 | Grassl . |
| 3,135,256 | 6/1964 | Gruber . |
| 3,164,151 | 1/1965 | Nicoll . |
| 3,220,406 | 11/1965 | Connelly . |
| 3,285,243 | 11/1966 | Yellin . |
| 3,285,244 | 11/1966 | Cottrell . |
| 3,295,516 | 1/1967 | Grassl . |
| 3,306,284 | 2/1967 | McKinley . |
| 3,313,297 | 4/1967 | Applegate et al. . |
| 3,320,950 | 5/1967 | McElvenny . |
| 3,343,532 | 9/1967 | Zumaglini . |
| 3,364,926 | 1/1968 | Alderson . |
| 3,374,785 | 3/1968 | Gaylord, Jr. . |
| 3,397,688 | 8/1968 | Gottfried . |

(List continued on next page.)

FOREIGN PATENT DOCUMENTS

| | | |
|---|---|---|
| 1132607 | 11/1968 | Australia . |
| 8112343 | 12/1982 | France . |
| 918770 | 2/1955 | Germany . |
| 1199921 | 9/1965 | Germany . |
| 2129140 | 12/1972 | Germany . |
| 2404683C3 | 8/1975 | Germany . |
| 3308571A1 | 9/1984 | Germany . |
| 3318938A1 | 11/1984 | Germany . |
| 3929347A1 | 3/1990 | Germany . |
| 3906233A1 | 8/1990 | Germany . |
| 3905115A1 | 8/1990 | Germany . |
| 2049436 | 12/1980 | United Kingdom . |
| 2165157 | 4/1986 | United Kingdom . |
| 2165762 | 4/1986 | United Kingdom . |
| 2182851 | 5/1987 | United Kingdom . |
| 2233900 | 1/1991 | United Kingdom . |
| 2234905 | 2/1991 | United Kingdom . |

Primary Examiner—Michael A. Brown
Attorney, Agent, or Firm—Levy, Zito & Grandinetti

[57] ABSTRACT

An improved cervical collar having an elongated neck encircling band secured to a two-piece chin support brace wherein each end of each of the two pieces of the chin support brace are permanently secured to the elongated encircling band body.

14 Claims, 3 Drawing Sheets

U.S. PATENT DOCUMENTS

| | | | |
|---|---|---|---|
| 3,504,667 | 4/1970 | McFarlane . | |
| 3,507,273 | 4/1970 | Yellin . | |
| 3,512,523 | 5/1970 | Barnett . | |
| 3,530,853 | 9/1970 | Bond . | |
| 3,572,328 | 3/1971 | Bond . | |
| 3,696,810 | 10/1972 | Gaylord, Jr. . | |
| 3,724,452 | 4/1973 | Nitschke . | |
| 3,756,226 | 9/1973 | Calabrese et al. . | |
| 3,850,164 | 11/1974 | Hare . | |
| 3,905,362 | 9/1975 | Eyrick et al. . | |
| 3,916,884 | 11/1975 | Attenburrow . | |
| 3,916,885 | 11/1975 | Gaylord, Jr. . | |
| 3,921,626 | 11/1975 | Neel . | |
| 3,964,474 | 6/1976 | Fox . | |
| 4,041,940 | 8/1977 | Frankel et al. . | |
| 4,043,325 | 8/1977 | Ochs et al. . | |
| 4,141,368 | 2/1979 | Meyer . | |
| 4,194,501 | 3/1980 | Watt . | |
| 4,204,529 | 5/1980 | Cochrane . | |
| 4,232,663 | 11/1980 | Newton . | |
| 4,299,209 | 11/1981 | Behrens et al. . | |
| 4,325,363 | 4/1982 | Berkeley . | |
| 4,383,523 | 5/1983 | Schurman . | |
| 4,401,111 | 8/1983 | Blackstone . | |
| 4,413,619 | 11/1983 | Garth . | |
| 4,515,153 | 5/1985 | Calabrese . | |
| 4,520,801 | 6/1985 | Lerman . | |
| 4,538,597 | 9/1985 | Lerman . | |
| 4,543,947 | 10/1985 | Blackstone . | |
| 4,562,833 | 1/1986 | Pujals, Jr. . | |
| 4,582,051 | 4/1986 | Greene et al. . | |
| 4,589,407 | 5/1986 | Koledin et al. . | |
| 4,628,913 | 12/1986 | Lerman . | |
| 4,643,174 | 2/1987 | Horiuchi . | |
| 4,643,719 | 2/1987 | Garth et al. . | |
| 4,702,233 | 10/1987 | Omicioli . | |
| 4,708,129 | 11/1987 | Pujals, Jr. . | |
| 4,712,540 | 12/1987 | Tucker | 602/18 |
| 4,782,824 | 11/1988 | Davies | 602/18 |
| 4,794,917 | 1/1989 | O'Leary . | |
| 4,819,622 | 4/1989 | Taylor et al. . | |
| 4,827,915 | 5/1989 | Gorsen . | |
| 4,886,052 | 12/1989 | Calabrese . | |
| 4,940,043 | 7/1990 | Burns | 602/18 |
| 4,955,368 | 9/1990 | Heimann . | |
| 4,969,453 | 11/1990 | Heimann . | |
| 4,987,891 | 1/1991 | Gaylord, Jr. et al. . | |
| 5,003,968 | 4/1991 | Mars . | |
| 5,005,563 | 4/1991 | Veale . | |
| 5,005,564 | 4/1991 | Grundei et al. . | |
| 5,010,877 | 4/1991 | Druskoczi . | |
| 5,029,577 | 7/1991 | Sarkozi . | |
| 5,038,759 | 8/1991 | Morenstern . | |
| 5,048,509 | 9/1991 | Grundei et al. . | |
| 5,054,475 | 10/1991 | Calabrese et al. . | |
| 5,058,572 | 10/1991 | Schmid et al. . | |
| 5,060,637 | 10/1991 | Schmid . | |
| 5,083,553 | 1/1992 | Stevenson . | |
| 5,097,824 | 3/1992 | Garth . | |
| 5,163,941 | 11/1992 | Garth et al. . | |
| 5,171,296 | 12/1992 | Herman . | |
| 5,180,361 | 1/1993 | Moore . | |
| 5,211,185 | 5/1993 | Garth et al. . | |
| 5,215,517 | 6/1993 | Stevenson | 602/18 |

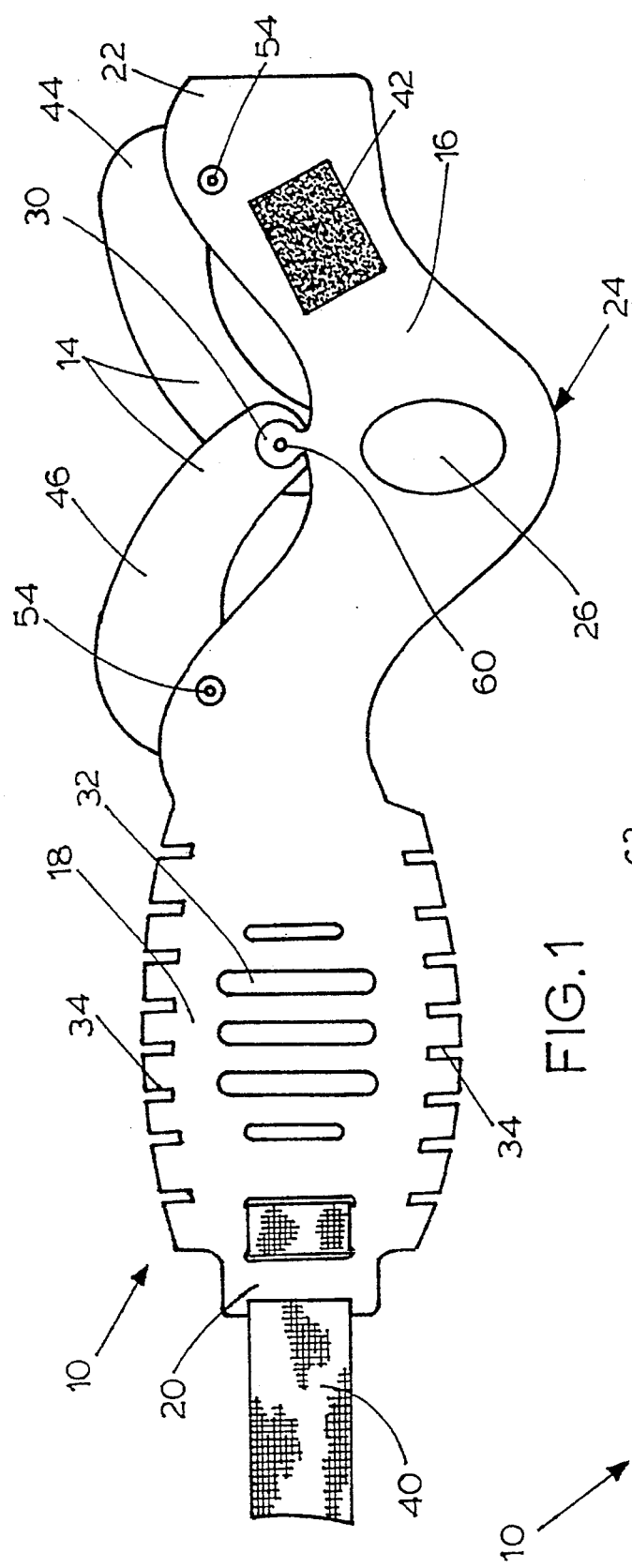
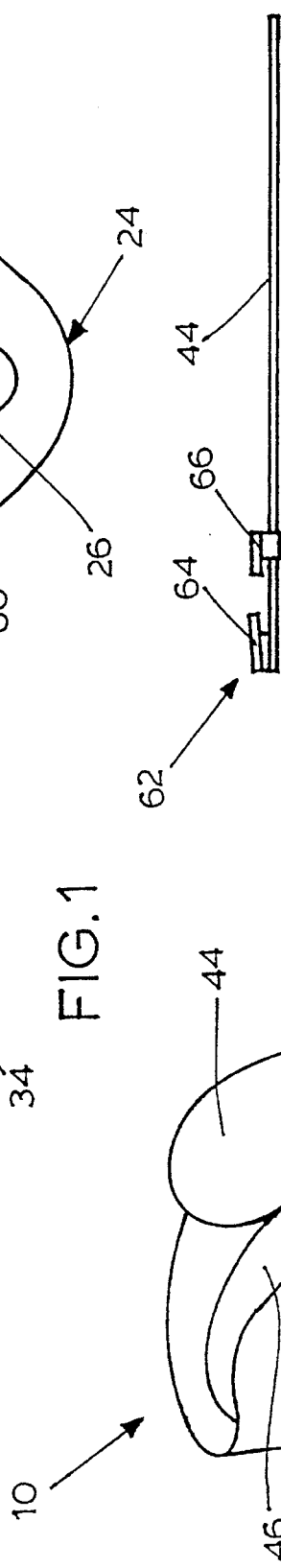

CERVICAL COLLAR

This application is a continuation application of U.S. application Ser. No. 08/237,139, filed May 3, 1994, now abandoned, which is a continuation application of U.S. application Ser. No. 08/064,221, filed on May 20, 1993, now U.S. Pat. No. 5,366,438.

BACKGROUND OF INVENTION

1. Field of Invention

This invention relates to cervical collars. More specifically this invention relates to a cervical collar with an improved chin support brace.

2. Prior Art

Numerous types of cervical collars have been disclosed which restrict the movement of the head and neck of a person who has suffered a neck or spinal injury. In fact, cervical collars are now standard equipment for emergency medical service squads and rescue units.

Originally, cervical collars were constructed of a relatively heavy strap formed from materials such as leather or other such heavy duty materials and usually included a number of metal braces. See, for example, U.S. Pat. No. 3,027,894. These heavy duty strap cervical collars were reasonably successful in immobilizing the head but presented significant problems when x-rays were needed because of the metal contained within the braces. In addition, these bulky cervical collars did not provide access to the patient's neck if a tracheotomy was necessary. Finally, because of the materials commonly used to manufacture these heavy-duty collars, they were cumbersome to use and expensive to produce. Because of current and anticipated limitations on the reuse of virtually all medical products, expense is a significant factor in the choice of all medical equipment, including cervical collars. Thus, these heavy duty cervical collars are too expensive as single use, medical products.

As a result of the enhanced utilization of lighter weight, plastic materials, cervical collars are now generally constructed from relatively stiff, light weight plastic materials that are capable of being bent to encircle the neck of the wearer and yet still provide substantial support for the wearer. Examples of these types of collars are disclosed, for example, in U.S. Pat. Nos. 5,083,553, 5,060,637 and Re. 32,219.

The U.S. Pat. No. Re. 32,219 patent discloses a rotatable, one-piece chin support brace as a key element of its cervical collar. This one-piece chin support brace is comprised of a relatively rigid, c-shaped, one-piece plastic piece joined to the body of the cervical collar at two fixed points, one point in the center of the chin support brace and the other point at one end of the chin support brace. In operation, the second end of this chin support brace, which is not permanently affixed to the body of the collar, is rotated upward. This rotation bends the chin support brace outward. After this outward bend is complete, the second end is secured to the body of the cervical collar by a rivet or snap fastener to form the in place, chin support brace.

The chin support brace of U.S. Pat. No. 5,083,553 is also both one-piece and generally c-shaped. However, this chin support brace is permanently secured at each end of its c-shape form to the body of the cervical collar by connecting pins. In use, the center of this chin support brace is rotated forward to permit the joining of a Velcro®, also known as hook and loop material, patch (54) on the lower portion of the chin support with another Velcro®, also known as hook and loop material, patch (52) on the body of the cervical collar to create the chin support brace.

While these chin support braces for cervical collars offer important improvements over the braces of prior cervical collars, each still has certain deficiencies making the utilization of the collar difficult.

Therefore it is an object of this invention to provide an improved cervical collar.

It is a further object of this invention to provide a cervical collar with an improved chin support brace for said collar.

It is a still further object of this invention to provide an improved cervical collar with a two-piece chin support brace.

It is a still further object of this invention to provide an improved cervical collar with a chin support brace which can be stored flat.

These and other objects and features of the present invention will become apparent to those skilled in the art from a consideration of the following detailed description, drawings and claims. The description, along with the accompanied drawings, provides a selected example of the construction of the device to illustrate the invention.

SUMMARY OF INVENTION

In accordance with the present invention there is provided an improved cervical collar comprised of an elongated neck encircling band and secured thereto a two-piece chin support brace with means for holding said chin support brace in a bowed forward position.

BRIEF DESCRIPTION OF DRAWINGS

This invention will now be described with reference to the accompanying drawings in which:

FIG. 1 is a front plan view of the cervical collar in its flat position.

FIG. 2 is a side perspective view of the improved cervical collar with the chin support brace in its bowed forward position as installed.

FIG. 4 is a side view of the j-shaped element of the two-part chin support brace of the improved cervical collar.

DETAILED DESCRIPTION OF THE PREFERRED EMBODIMENT

Figure 3:
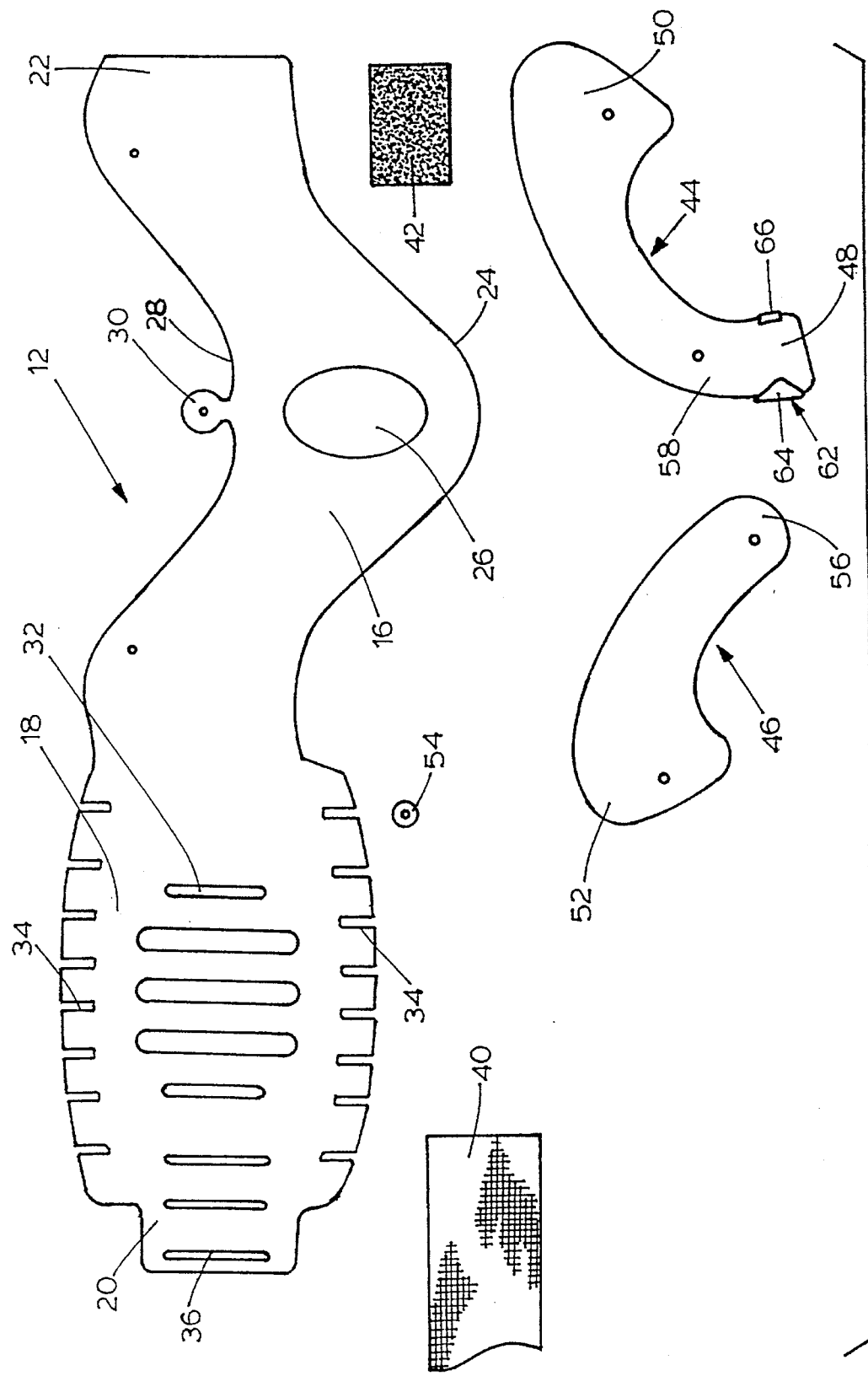
FIG. 3 is an exploded view of the improved cervical collar.

Although the invention is adaptable to a wide variety of uses, it is shown in the accompanying drawings for purposes of illustration as embodied in an improved cervical collar (10) comprised of an elongated neck encircling band (12) and secured thereto a two-piece chin support brace (14) with means for holding said chin support brace in a bowed forward position. See FIGS. 1 and 3.

The elongated neck encircling band (12) is formed from a stiff, plastic sheet material such as high density polyethylene, polyvinyl chloride or other such stiff, sturdy plastic material. The elements of the cervical collar may be die cut, extruded or prepared from molds as is conventional in the industry. For comfort there may be secured to the inner surface of this stiff plastic at various locations soft, foam type pads (not shown) which are comprised of conventional soft plastic material. These soft plastic pads are secured to the stiff plastic material by any conventional securing means such as an adhesive or snap fasteners. It is preferred that these foam pads be secured by cement or other adhesive to reduce the number of parts of the cervical collar (10).

The elongated neck encircling band (12) is preferably of one-piece construction generally comprised of a frontal portion (16), a back portion (18), a back side portions (20) and a front end portion (24). See FIG. 3. The elongated neck encircling band (12) is asymmetrical in design with the frontal portion (16) attached to, and an integral part of, the back portion (18).

The frontal portion (16), which has affixed to it the two-piece chin support brace (14), will be placed against the user of the cervical collar on the front portion of the user's neck under the user's chin. The back portion (18) of the cervical collar (10) is generally affixed to the back of the user's neck. The back side portion (20) and the front end portion (22) are integral elements of the neck encircling band (12) located at each end and are generally secured together after the improved cervical collar is secured to the wearer. See FIG. 2.

The frontal portion (16) when placed flat is generally curvilinear in design, curving downward and then back upward from the front end portion (22) to the back portion (18) with an opposite longitudinal curved edge which runs from one side of the frontal portion to the other side. See FIG. 1. The lower curved edge (24) of the frontal portion when in use rests against the chest of the wearer and has above it a cut out section (26) overlapping the larynx of the wearer to permit a tracheotomy to be performed through the cut out section (26) with the cervical collar (10) in place. The upper curved edge (28) of the frontal portion (16) runs roughly parallel to the lower curved edge (24).

Secured to the upper curved edge (28) is a chin support tab (30) extending upward away from the upper curved edge (28) of the frontal portion. This chin support tab (30) is used to secure the two-piece chin support brace (14) to the frontal portion (16) of the neck encircling band (12). See FIG. 3.

Secured to one side of the frontal portion and an integral part of the cervical collar is the back portion (18) of the cervical collar (10). The back portion (18) can be of any conventional shape from generally rectangle to generally oval. The back portion (18) of the elongated neck encircling band (12) contains a number of vertical elongated slots (32) and cooperating slits (34) to make the neck encircling band (12) more flexible. These slots (32) are generally cut out sections contained in the body of the back portion (18) running horizontally from near where the frontal portion (16) joins the back portion (18) to the opposite side of the back portion. These slots (32) are generally located in the body of the back portion (18) running approximately half way the distance between the top and the bottom of the back portion (18). See FIGS. 1 and 3. The height and width of these slots is not critical but should be of sufficient size to permit enhanced flexibility and bending of the elongated neck encircling band (12). Preferably these slots are at least about 2 inches in height and about ¼ inch in width.

The cooperating slits (34) are inscribed into the top and bottom edges of the back portion (18) and extend part of the way into the back portion. The extent of the extension of these slits (18) is not critical although it should not reach the slots (32). The slits (34) preferably are at least about a ½ to 1 inch or so in length. These slots (32) and slits (34) should be arranged in such a manner as to provide adequate flexibility and bendability to the back portion (18) of the elongated neck encircling band (12) without impacting on the structural integrity of the cervical collar (10).

An integral part of the back portion (18) located distal from the frontal portion (16) is the back side portion (20). This back side portion (20) is generally an elongated tab extending from the body of the back portion, and integrally connected to the back portion (18). In an alternative embodiment the back side portion (18) merges into the back portion and is eliminated as a discrete element of the device. A number of elongated slots (36) similar to those contained in the body of the back portion (18) may be provided in this back side portion (20). Distal from the back side portion (20) of the elongated neck encircling band (12) is the front end portion (22) which extends out from the frontal portion (16). It acts in concert with the back side portion (20) when the cervical collar is placed around a user's neck. The frontal end portion (22) is also generally only a tab of generally rectangular shape extending from the body of the frontal portion (16) of the cervical collar. In an alternative embodiment the front end portion (22) merges into the frontal portion (16) and is eliminated as a discrete element of the device. A collar retaining means (30) is added to the elongated encircling band to assist in the securing of the back side portion (20) to the front end portion (22) to hold the improved cervical collar (10) securely in place.

The collar retaining means can be any choice of straps or fasteners which will hold the improved cervical collar (10) together. For example, in a preferred embodiment an elongated strip of Velcro® (40), also known as hook and loop material, is secured to the back portion (18) and the back side portion (20) of the cervical collar through selected elongated slots (36) on the back side portion (20) and also the body of the back portion. See FIG. 1. Corresponding Velcro®, also known as hook and loop material, fasteners (42) which interact with the Velcro®, also known as hook and loop material, strip (40) are secured to the surface of the frontal end portion (22) and the front portion (16) by conventional securing methods, such as adhesives, to permit the Velcro®, also known as hook and loop material, strip (40) when encountering the Velcro®, also known as hook and loop material, fasteners (42) to hold the improved cervical collar (10) securely in place.

Figure 5:
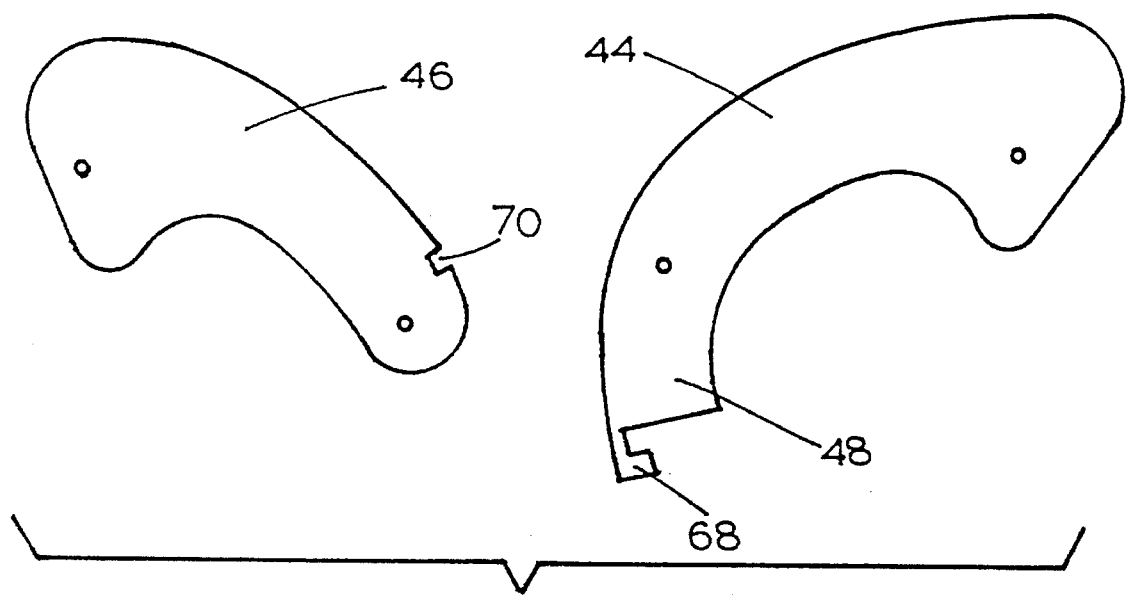
FIG. 5 is a side view of the j-shaped element of the chin support brace showing an alternative locking device.

The second major element of the improved cervical collar (10) is the two-piece chin support brace (14). The two pieces of the chin support brace are the j-shaped element (44) and the curved element (46). See FIGS. 3 and 5. They are constructed from the same types of stiff plastic material as is the elongated neck encircling band (12). The j-shaped element (44) and the curved element (46) are similar in construction except the j-shaped element has an additional end section (48) which extends the length of the j-shaped element. The second end (50) of the j-shaped element which is distal from the end section (48) and the second end (52) of the curved element (46) are secured at separate locations to the back side of the frontal portion (16) of the elongated neck encircling band. See FIG. 1. These two second ends are held securely in place by any conventional securing means such as a pin which extends through the surface of the elongated neck encircling band (12) and through the appropriate second ends of the j-shaped element (44) and the curved element (46). They can be permanently secured in place, for example, by rivets or snap fasteners (54).

The curved element (40) and the j-shaped element (44) are also secured to the chin support tab (30) of the frontal portion (16). The first end (56) of the curved element and a portion (58) of the j-shaped element (44), which portion is located close to the end section (48) of the j-shaped element (44), are secured to the chin support tab (30) of the frontal portion (16) of the elongated neck encircling band (12). See FIGS. 1 and 3. They are secured to the chin support tab (30) by a securing device (60) similar to the securing devices (54) used to secure the second end (50) of the j-shaped element and the second end (52) of the curved portion to the frontal portion (16). This second securing device (60) may be a pin, rivet or snap fastener. However, whichever second securing device (60) is chosen, it is required that this second securing device (60) permit rotation of the j-shaped element (44) and curved element (46) about the axis of the second securing device (60) secured to the chin support tab (30).

Secured to the end section (48) of the j-shaped element (44) is the means for holding the chin support brace in a bowed forward position. Preferably the means for holding is a locking device (62) for locking the two elements of the chin support brace together in a bowed forward position after they are rotated about the axis of the chin support tab (30). See FIG. 4. When each of these elements of the chin support brace are rotated about the axis of the tab, the end section (48) of the j-shaped element (44) rotates upward and forward until its top edge is above the top edge of the curved element (46). As both rotate, the top surface of each of the chin support elements bows forward to provide the support for the chin of the wearer. See FIG. 2. As these chin support elements are rotated, each side of the frontal end portion (16) will also rotate backward to form the frontal support of the improved cervical collar. After both the j-shaped element (44) and the curved elements (46) are rotated to their bowed forward position, the locking device (62) holds them in this bowed forward position. In a preferred embodiment this locking device (62) is a c-shaped locking device element with a top hook portion (64) and a bottom snap portion (66) which are integral parts of the j-shaped element. See FIG. 4. The second end (56) of the curved chin support element hooks under the top hook portion (64) of the c-shaped locking device and above the bottom snap portion (66). The top of the curved chin support slides under the top hook portion (64) of the locking device and snaps in place under the bottom snap portion (66) of the locking device (62) to hold the two piece chin support brace in its bowed forward position.

In an alternative preferred embodiment, the means for holding the chin support brace in a bowed forward position is comprised of a hook and tab piece (68) secured to the j-shaped element (44) which will fit into a slot (70) in the second end of the curved element (46) to hold the chin support elements in their bowed forward position. See FIG. 5.

In operation, when the improved two-piece cervical collar (10) is to be used, the j-shaped (44) and the curved chin support (46) elements are rotated about the chin support tab (30) of the frontal portion (16) and are secured in a bowed position by use of either the c-shaped locking device (62) or the lock, tab and slot arrangement (68, 70). This results in the chin support brace (14) being bowed forward to more easily support the wearer's chin. As the j-shaped (44) and the curved chin support (46) elements are bowed forward, the frontal portion (16) bows backward. Holding the frontal portion (16) in place against the user's neck and chest, the back portion (18) is wrapped around the back of the user's neck. The collar retaining element such as an elongated strip (40) of Velcro®, also known as hook and loop material, which is attached to the back side portion (20) is secured firmly in place against one or more Velcro®, also known as hook and loop material, fasteners (42) which are secured to the frontal end portion (22) and, if necessary, on to the top surface of the frontal portion (16).

A cut out section (26) at the front of the frontal portion (16) is available for access to the larynx for a tracheotomy.

After the user no longer needs the cervical collar, the elongated Velcro®, also known as hook and loop material, strip (40) used as a collar retaining element (38) is removed from the fasteners (42) attached to the frontal portion (16) and the front end portion (22). If desired the j-shaped support element (44) can then be disengaged from the curved support element (40) to permit the entire cervical collar (10) to return to its generally flat position.

I claim:

1. A cervical collar comprising:

an elongated neck encircling band, said elongated neck encircling band having a collar retaining means;

a chin support brace secured to said elongated neck encircling band, said chin support brace having:

a first chin support element; and a second chin support element; said first chin support element and said second chin support element each has a first end and a second end, said first end of each of said first chin support element and said second chin support element is rotatably affixed to first and second locations on said elongated neck encircling band, said second end of said first chin support element rotatably overlaps and is affixed to said second end of said second chin support element; and a locking means secured to said chin support brace whereby rotation of said first chin support element and said second chin support element into an operable and locked position bows said chin support brace.

2. The cervical collar of claim 1 wherein said first chin support element is a j-shaped chin support element and said second chin support element is a curved chin support element.

3. The cervical collar of claim 2 wherein said first end of said j-shaped chin support element and said first end of said curved chin support element are both secured to a tab on said elongated neck encircling band extending upward from said elongated neck encircling band.

4. The cervical collar of claim 2 wherein said locking means is a c-shaped locking device element secured to a first end of said j-shaped chin support element.

5. The cervical collar of claim 2 wherein said locking means is a hook and tab piece provided as an integral part of a first end of said j-shaped chin support element operating in conjunction with a slot in an upper edge of a first end of said curved element.

6. The cervical collar of claim 1 wherein said elongated neck encircling band includes a frontal portion, a back portion, a frontal end portion, and a back side portion.

7. The cervical collar of claim 6 wherein said frontal portion has a lower and an upper curvilinear edge.

8. The cervical collar of claim 7 wherein said tab extending upward from said upper curvilinear edge is secured to said upper curvilinear edge of said frontal portion.

9. The cervical collar of claim 1 wherein said collar retaining means releasably affixes to said elongated neck encircling band.

10. The cervical collar of claim 9 wherein said collar retaining means is a strap of hook and loop material.

11. A cervical collar comprising:

an elongated neck encircling band having front, back, and first and second side portions and collar retaining means;

a chin support brace secured to said elongated neck encircling band, said chin support brace including first and second chin engaging support elements, each element having a curvilinear shape and first and second ends;

said first end of said first chin support element being rotatably coupled to said first side portion of said neck encircling band, said first end of said second chin support element being rotatably coupled to said second side portion of said neck encircling band, and said second end of each of said chin support elements being rotatably coupled together, whereby said first and second chin support elements arc rotatable with respect to each to define a lowered chin supporting configuration; and locking means on said chin support brace for limiting rotational movement of said first chin supporting element with respect to said second chin supporting element to form said bowed chin supporting configuration.

12. The cervical collar of claim 11, wherein said second ends of said first and second chin support elements are rotatably coupled to said neck encircling band.

13. The cervical collar of claim 11, wherein said front portion of said neck encircling band includes a tab portion, and said second ends of said first and second chin support elements being rotatably coupled to said tab position.

14. The cervical collar of claim 11, wherein said locking means locks said first and second chin support elements together to define a substantially continuous curvilinear chin support.

* * * * *